(12) United States Patent
Barve et al.

(10) Patent No.: US 8,674,131 B2
(45) Date of Patent: Mar. 18, 2014

(54) PROCESS FOR PREPARATION OF PURE ALKYL ESTERS FROM ALKALI METAL SALT OF CARBOXYLIC ACID

(75) Inventors: Prashant Purushottam Barve, Pune (IN); Bhaskar Dattatraya Kulkarni, Pune (IN); Milind Yashwant Gupte, Pune (IN); Sanjay Narayan Nene, Pune (IN); Ravindra William Shinde, Pune (IN)

(73) Assignee: Council of Scientific and Industrial Research (IN)

( * ) Notice: Subject to any disclaimer, the term of this patent is extended or adjusted under 35 U.S.C. 154(b) by 0 days.

(21) Appl. No.: 13/394,768

(22) PCT Filed: Sep. 6, 2010

(86) PCT No.: PCT/IB2010/002203
§ 371 (c)(1),
(2), (4) Date: Aug. 2, 2012

(87) PCT Pub. No.: WO2011/027211
PCT Pub. Date: Mar. 10, 2011

(65) Prior Publication Data
US 2012/0296110 A1    Nov. 22, 2012

(30) Foreign Application Priority Data
Sep. 7, 2009  (IN) ............................ 1842/DEL/2009

(51) Int. Cl.
*C07C 69/88*    (2006.01)
*C07C 69/68*    (2006.01)
*C07C 67/00*    (2006.01)

(52) U.S. Cl.
USPC ............................. 560/75; 560/179; 560/265

(58) Field of Classification Search
CPC ...................................................... C07C 69/68
See application file for complete search history.

(56) References Cited

U.S. PATENT DOCUMENTS

| | | | |
|---|---|---|---|
| 2,290,926 | A | 7/1942 | Weisberg |
| 2,334,524 | A | 11/1943 | Wenker |
| 2,350,370 | A | 6/1944 | Schopmeyer |
| 2,390,140 | A | 12/1945 | Weisberg |
| 2,406,648 | A | 8/1946 | Weisberg |
| 2,434,300 | A | 1/1948 | Weisberg |
| 5,453,365 | A | 9/1995 | Sterzel |
| 6,342,626 | B1 | 1/2002 | Kaimal |

FOREIGN PATENT DOCUMENTS

| | | |
|---|---|---|
| DE | 171835 C | 3/1905 |
| DE | 4341770 A1 | 6/1995 |
| WO | 97/30964 A1 | 8/1997 |

OTHER PUBLICATIONS

Zaragoza Dorwald, Side Reactions in Organic Synthesis, 2004, Wiley-VCH Verlag GmbH & Co. KGaA, Weinheim, Preface. p. IX.*
International Application No. PCT/IB2010/002203 International Search Report and Written Opinion dated Feb. 18, 2011.
International Application No. PCT/IB2010/002203 International Preliminary Report on Patentability dated Dec. 12, 2011.
Holten, C.H., "Lactic Acid, Properties and Chemistry of Lactic Acid Derivatives", printer: Oswald Schmidt KG Leipzig, 1971, p. 149.

* cited by examiner

*Primary Examiner* — Paul A Zucker
(74) *Attorney, Agent, or Firm* — Banner & Witcoff, Ltd.

(57) ABSTRACT

The dehydrated alkali metal salts of carboxylic acid are dissolved in the alcohol such as methanol or ethanol or butanol to make their solution in corresponding alcohol. The solution alcohol is further treated with carbon dioxide under pressure or at atmospheric pressure at elevated temperature such as 150 to 200° C. The carboxylic acid gets converted into corresponding alkyl ester and calcium carbonate or sodium carbonate or potassium carbonate as the byproduct. Calcium lactate or sodium lactate or sodium acetate or sodium benzoate or sodium salicylate as alkali metal salt solution prepared in methanol or ethanol or butanol when treated with carbon dioxide under pressure or at atmospheric pressure at elevated temperature gets converted to methyl lactate or ethyl lactate or methyl acetate or methyl benzoate or methyl salicylate as product.

10 Claims, 5 Drawing Sheets

PROCESS FOR PREPARATION OF PURE ALKYL ESTERS FROM ALKALI METAL SALT OF CARBOXYLIC ACID

CROSS REFERENCE TO RELATED APPLICATIONS

This is a U.S. National Phase Application under 35 U.S.C. §371 of International Application No. PCT/IB2010/002203, filed Sep. 6, 2010, which was published under PCT Article 21(2) and claims priority to Indian Patent Application No. 1842/DEL/2009, filed Sep. 7, 2009, the entire contents of which are incorporated herein by reference in their entireties for any and all non-limiting purposes.

FIELD OF THE INVENTION

Present invention provides a process for the preparation of pure alkyl esters from corresponding alkali metal salts of carboxylic acid using carbon dioxide and alcohol. The alkali metal carboxylate salts are prepared from natural sources by a process of fermentation or by synthesis.

BACKGROUND OF THE INVENTION

Highly pure S-(−)-methyl lactate constitutes an important product having interesting possibilities of application at an industrial level. It can be used in pharmaceuticals and in the production of high purity lactic acid. The lactic acid so produced can be used in the production of dairy products, as an acidulating agent in the alimentary field, as an intermediate for the production of plasticizer agents, adhesives, pharmaceutical products, in the production of lactates, as a mordant in wool dying and many others. Similarly, the high purity lactic acid prepared from high purity methyl lactate has considerable prospects of industrial development in the field of production of biocompatible and biodegradable polymers which are useful for manufacturing bags, application films, in the field of sanitary and medical applications and so on.

The manufacturing method for methyl lactates as known from prior art, in general, comprises of two steps. In step 1, alkali metal lactate is reacted with concentrated or dilute sulfuric acid. The alkali metal sulfate is produced as the side product along with the dilute aqueous solution of lactic acid. In step 2, dilute lactic acid solution is concentrated and esterified with methanol using a catalyst. The resultant mixture of methyl lactate, methanol and water is further purified to give product i.e. methyl lactate. Various methods of manufacturing methyl lactate based on the above general method have been suggested in the past as cited in the following patented literatures: Reference may be made to U.S. Pat. Nos. 2,290,926, 2,406,648, 2,390,140, 2,334,524, 2,350,370 and 2,434,300, wherein a method for manufacture of methyl lactate has been disclosed, but suffer from various drawbacks such as impure product, need for expensive and energy intensive processes for separation of product, residue of sodium sulphate, corrosiveness and several others.

References may be made to U.S. Pat. No. 6,342,626, wherein method for manufacture of methyl lactate from 73% lactic acid in two stages at high temperature 200° C. and high pressure of 20 kg/cm² is described. The process is carried out in two stages; first stage equilibrium conversion of lactic acid reported is about 80% and after isolating byproducts of the first stage, the second stage gives remaining conversion of lactic acid. The drawbacks are the use of higher temperature and pressure and corrosive nature of lactic acid increases the cost of the commercial manufacturing setup. Further drawback is that, the lactic acids can recemize at such higher temperature (C. H. Holtan, Lactic Acid, properties and chemistry of lactic acid derivatives, Printer Oswald Schmidt KG Leipzig, 1971, page 149). Further, the optical purity of methyl lactate and the chemical purity of methyl lactate produced are not reported.

References may be made to U.S. Pat. No. 5,453,365, wherein a continuous process for the preparation of lactates by fermentation of mixtures containing sugars, conversion of the lactic acid obtained during fermentation to its salts, followed by esterification is disclosed, in which:
a) An alkaline earth metal carbonate or bicarbonate is added to the fermentation liquor so as to neutralize the resultant lactic acid to a degree of at least 90 mol %,
b) The resulting fermentation liquor is adjusted to pH 7 to 13 by the addition of $NH_3$ and $CO_2$ and the resultant precipitates are separated, and
c) The resulting, purified ammonium lactate solution is esterified with an alcohol.

The general method of preparation of methyl lactate reported in the prior art is by the acidification of alkali metal lactate to generate crude lactic acid and alkali metal sulfate as the byproduct, followed by esterification of crude lactic acid by co-current method of reactive distillation where, the product methyl lactate, byproduct water and excess alcohol is taken out of reactive distillation still by maintaining the still at higher temperature. This leads to the accumulation of the acidity at the reactive distillation still and gives rise to the undesired byproducts like hydroxyl methyl furfural, 2-pentene-1-ol etc. It is known that in the product mixture of alcohol, water and methyl lactate obtained from the co-current reactive distillation, methyl lactate forms an azeotrope with water, the isolation of methyl lactate in pure anhydrous form from the mixture of alcohol, water and methyl lactate is difficult. In the prior art reported, there is no mention of the impurity profile of the product and its optical purity. Further to it, the reported methods use alkali metal lactates to produce crude lactic acid and produce waste alkali metal sulfate. Further drawback of reported methods are that the crude lactic acid generated after reacting alkali metal lactate with sulfuric acid and maintained at very low pH value, the crude lactic acid being very corrosive in nature and at high temperature it is more corrosive in nature, the manufacturing setup and it's material of construction needs to be selected carefully and it is very capital intensive in nature. Further drawback of these reported methods are that the alkali metal is wasted as alkali metal sulfate and the alkali can not be recycled to the fermentation section where alkali metal lactates are produced.

OBJECTIVE OF THE INVENTION

The main objective of the present invention is to provide a process for the preparation of pure alkyl esters by direct esterification of alkali metal carboxylate salts of calcium, sodium, or potassium using an alcohol such as methanol or ethanol and carbon dioxide. Another object of the present invention is to provide a process for the preparation of alkyl esters without using mineral acid.

Still another object of the present invention is to provide pure methyl lactate by direct esterification of calcium lactate or sodium lactate or potassium lactate and recycle the byproduct of the reaction namely calcium bicarbonate or sodium bicarbonate or potassium bicarbonate in sugar cane juice fermentation process to make corresponding alkali metal lactate.

Yet another object of the present invention is to provide pollution free process for production of pure methyl lactate and pure lactic acid by avoiding formation of calcium sulfate or sodium sulfate or potassium sulfate.

Still another object of the present invention is to get pure methyl lactate which can be hydrolyzed with or without using catalyst to get pure lactic acid.

SUMMARY OF THE INVENTION

Accordingly, present invention provides a single step process for the preparation of optically pure alkyl esters by esterification of alkali metal salts of carboxylic acid using alcohol and $CO_2$ and the said process comprising the steps of:
i. mixing dehydrated metal carboxylate salt powder with methanol for period in the range of 15 minutes to 30 minutes with stirring in the range of 500 to 1000 rpm to obtain 5-30% by wt solution of metal carboxylate salt in methanol;
ii. pressurizing solution as obtained in step (i) with carbon dioxide in the range of 20-60.4 $Kg/cm^2$ at temperature in the range of 145 to 165° C. for period in the range of 15 minutes to 1 hour to obtain alkyl ester and by products as precipitate;
iii. separating precipitates as obtained in step (ii) by filtration which is recycled in fermentation section to get alkali metal salt from glucose source;
iv. repeating the steps (i) (ii) and (ii) preferably 3 to 4 times till desired conversion of alkali metal salt to alkyl ester with separate byproducts;
v. recovering the alkyl ester by distillation with purity in the range of 99.50 to 99.8% by wt. with about 0.03-0.1% by wt of moisture from filtrate unreacted methanol being recovered and recycled.

In an embodiment of the present invention, said byproducts are corresponding alkali metal carbonate or bicarbonate.

In another embodiment of the present invention, metals are selected from the group consisting of sodium, potassium or calcium.

In yet another embodiment of the present invention, carboxylate salt of metals are selected from the group consisting of acetates, lactates, salicylates or benzoates.

In yet another embodiment of the present invention, alcohol used is selected from the group consisting of methanol, ethanol and butanol.

In yet another embodiment of the present invention, optical purity of alkyl esters is ranging between 98 to 99%.

In yet another embodiment of the present invention, process is carried out in batch or continuous modes.

In yet another embodiment of the present invention, recycled methanol used for the process in step (b) is in the mole ratio of 2.8:1 to 4:1, preferably 2.8 to 1 with alkali metal salt.

In yet another embodiment of the present invention, conversion percentage of metal carboxylate salt into alkyl esters is in the range of 95 to 99%.

In yet another embodiment of the present invention, yield of the reaction is ranging between 90 to 99.0% and the selectivity of the reaction towards alkyl esters is in the range of 99.0%.

In yet another embodiment of the present invention, the alkali metal carbonates or bi-carbonates are recycled in fermentation section to get alkali metal carboxylic acid salt from glucose source.

In yet another embodiment of the present invention, recovery of alkyl esters by distillation is optionally done using vacuum.

In yet another embodiment of the present invention, alkali and alkaline earth metal salts are sourced from natural and optionally from non natural sources.

In yet another embodiment of the present invention, alkali metal carboxylate salts are prepared from natural sources by a process of fermentation or by synthesis.

In yet another embodiment of the present invention, process for the preparation of alkyl esters is carried out without using mineral acid.

In yet another embodiment of the present invention, byproducts are recycled of the reaction namely calcium bicarbonate or sodium bicarbonate or potassium bicarbonate in sugar cane juice fermentation process to make corresponding alkali metal lactate.

In yet another embodiment of the present invention, present invention provides pollution free process for production of pure methyl lactate and pure lactic acid by avoiding formation of calcium sulfate or sodium sulfate or potassium sulfate.

In yet another embodiment of the present invention, present invention provides pure methyl lactate which can be hydrolyzed with or without using catalyst to get pure lactic acid.

DETAILED DESCRIPTION OF THE INVENTION

The process of the invention comprises a single step direct esterification of dehydrated alkali metal carboxylate salts using carbon dioxide and an alcohol, preferably methanol to obtain optically pure alkyl ester. The process involves a procedure for preparation of dehydrated alkali metal carboxylate salts, reacting under reflux for a period of about 1 hr, followed by distillation to obtain the desired pure alkyl ester having purity of about 99.8% by wt, moisture of 0.03-0.1% by weight, unreacted methanol being recovered and recycled.

The Process Comprises the Steps of:
(a) reacting dehydrated alkali metal carboxylate salt powder with methanol in desired stoichiometric ratio so as to get 5-30% solution in methanol, pressurizing with carbon dioxide in the range of 20-60 $Kg/Cm^2$ at temperature range of 145 to 165° C. up to one hour to obtain alkyl ester and corresponding alkali metal carbonate or bi-carbonate as precipitate;
(b) Separation of said precipitates of alkali metal carbonate or bi-carbonate by filtration which is recycled in fermentation section to get alkali metal salt from glucose source;
(c) repeating the above procedure mentioned in steps (a) and (b) preferably 3 to 4 times, till desired conversion of alkali metal salt to alkyl ester are obtained with separate alkali carbonate or bi-carbonate precipitates and (d) Recovery of reasonably pure alkyl ester (<99.5%) from filtrate obtained in above steps.

The pure alkyl ester thus obtained may optionally hydrolyzed to get pure lactic acid.

The process of the present invention is operable optionally in batch or continuous modes.

The alkali metals are selected from sodium, potassium, calcium and such like.

The salts of alkali metal are selected from acetates, lactates, salicylates, benzoates and such like.

The recovery of alkyl esters by distillation is optionally done using vacuum.

The recycled methanol used for the process in step (b) is in the mole ratio of 2.8:1 to 4:1, preferably 2.8 to 1 with alkali metal salt.

The purity of alkyl ester obtained is in the range of 99.50 to 99.8% by wt. with about 0.03-0.1% by wt of moisture.

The yield of the reaction is greater than 99.0% and the selectivity of the reaction towards alkyl esters is greater than 99.0%.

The optical purity of the alkyl esters obtained according to the invention is greater than 99.0%

Alkali and alkaline earth metal salts are sourced from natural resources. In one embodiment of the invention, they can also be obtained from non natural sources.

Highly pure lactic acid thus obtained by the process of the invention is used as a monomer for making polylactic acid, as a monomer to prepare biodegradable polymer, as an acidulant, as a food additive and for pharmaceutical applications where as methyl lactate can be used as solvent, also has pharmaceutical applications.

EXAMPLES

The following examples are given by way of illustration only and therefore should not be constrained to limit the scope of the present invention.

Direct Esterfication of Calcium Lactate at High Pressure

Example-1

Dehydration of Calcium Lactate Powder

Calcium lactate powder obtained from sugar cane juice fermentation or any other sucrose source was dried under vacuum (50 mbar) and at 80° C. temperature using vacuum dryer for 24 hrs. The initial moisture content in calcium lactate was 30% and the moisture in calcium lactate was reduced to 1.5% by wt. This dry calcium lactate powder was used in subsequent examples given below.

Example-2

Preparation of Feed Stock Solution for Reaction

The mild steel high pressure reactor vessel having capacity of 5 L, was charged with 250 g dry calcium lactate powder as mentioned in Example-1 along with 2250 g pure methanol so as to get final 10% by wt solution of calcium lactate in pure methanol, The material is then continuously mixed at 750 RPM using agitator for 15 min at ambient temperature to get calcium lactate solution in methanol. This crude calcium lactate solution in methanol was used as feed stock in the subsequent Examples given below.

Example-3

Figure 1:
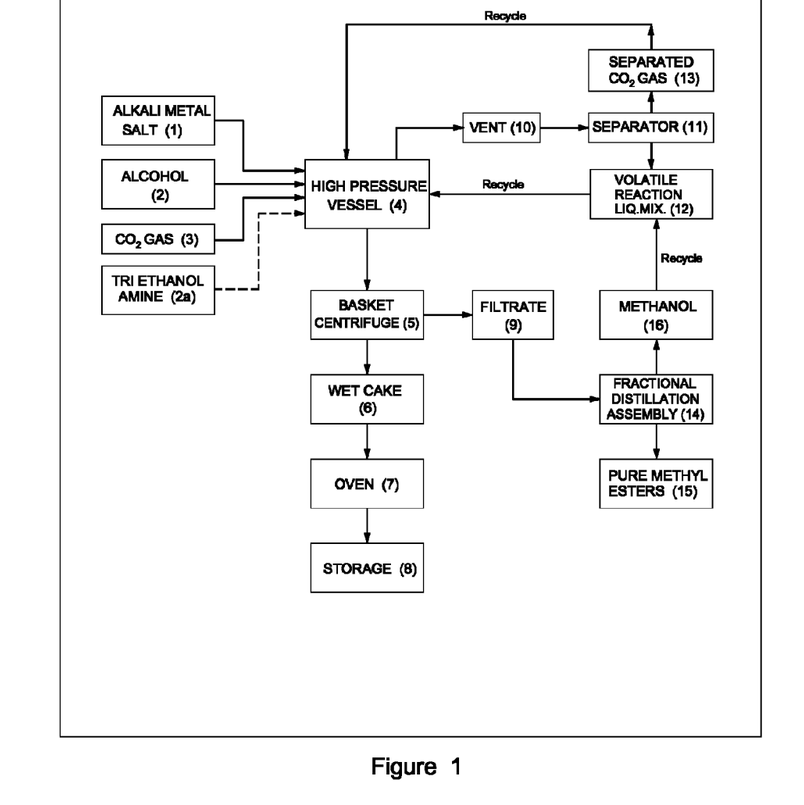
FIG. 1: Batch process for the synthesis of alkyl esters using alkali metal salt of carboxylic acid, alcohol and $CO_2$ gas in high pressure reactor with number of recycle of alcohol and $CO_2$ gas.

Direct Esterification of Calcium Lactate Solution in Methanol with Carbon Dioxide at 165° C. at High Pressure (FIG. 1)

10 wt % (1100 g) dilute calcium lactate solution (1) in methanol (2) prepared as explained in Example-2 was charged in mild steel high pressure reactor (4) having capacity of 5 L and continuously stirred at 750 RPM using agitator. Carbon dioxide (3) gas from cylinder was pressurized in reactor so as to get initial pressure 20 Kg/cm$^2$. Reaction material was then allowed to heat till 165° C. and was maintained at this temperature for 1 hour. During operation pressure inside reactor get revised till 60.4 Kg/cm$^2$. Reaction mass was then allowed to cool till 25° C. and the reaction mixture was filtered on the basket centrifuge (5) at 3000 RPM. The wet cake (6) obtained from centrifuge; containing calcium carbonate was allowed to dry in oven (7) at 110° C. and stored (8). The filtrate (9) collected from centrifuge was analyzed for methyl ester, methanol contents using Shimadzu made GC-MS Model-QP5000 where as the moisture was measured by Automatic Karl-Fischer, Lab India made instrument. The concentration of methyl ester in filtrate was found to be 7.5% by wt where as methanol concentration was 92.4% by wt. and moisture content by Karl-Fischer method was 1.1% by wt. After desired operation time, pressure inside reactor (4) was released through vent (10), vapors were passed to separator (11) where carbon dioxide gas (13) was separated, which can be recycled at (4), from other volatile reaction liquid mixture (12) which was recycled at (4).

In second stage, filtrate (9) obtained from above said centrifuge was again charged in the same mild steel high pressure reactor (4) and continuously stirred at 750 RPM for 15 minutes using agitator. Again carbon dioxide gas (3) was bubbled in the reactor to reach a pressure in the reactor till 40 Kg/cm$^2$. Reaction material was then allowed to heat till 165° C. and was maintained at this temperature for 1 hour. During operation the pressure inside reactor gets raised to 59.0 Kg/cm$^2$. Reaction mass was then allowed to cool till 25° C. and then the reaction mixture was filtered on the basket centrifuge (5) at 3000 RPM. The wet cake (6) obtained from centrifuge (5), containing calcium carbonate was allowed to dry in oven at 110° C. (7) and stored (8). Filtrate collected (9) from centrifuge was analyzed for methyl ester, methanol and moisture contents as above. The concentration of methyl ester in filtrate was found to be 9.3% % by wt where as methanol concentration was 90.1% by wt. and moisture content by Karl-Fischer method was 1.0% by wt. After desired operation time, pressure inside reactor (4) was released through vent (10) vapors were passed to separator (11) where carbon dioxide gas (13) was separated, from other volatile reaction liquid mixture (12). The carbon dioxide so separated can be recycled at (4) while the liquid mixture can be recycled at (4).

In third stage, filtrate obtained from above mentioned second stage centrifuge was again charged in same mild steel high pressure reactor (4). Other operating procedure and parameters were same as per first and second stage. Final pressure obtained in reactor was found to be 55 Kg/cm$^2$. The concentration of methyl ester in filtrate (9) obtained from centrifuge (5) was found to be 10.4% by wt where as methanol concentration was 89.4% by wt. And moisture content by Karl-Fischer method was 1.0% by wt. After desired operation time, pressure inside reactor (4) was released through vent (10), vapors were passed to separator (11) where carbon dioxide gas (13) was separated, which can be recycled at (4), from other volatile reaction liquid mixture (12) which was recycled at (4).

In fourth stage, filtrate obtained from above mentioned third stage centrifuge was again charged in same mild steel high pressure reactor (4). Other operating procedure and parameters were same as per first, second and third stage. Final pressure obtained in the reactor was found to be 54.5

Kg/cm². The concentration of methyl ester in filtrate (9) obtained from centrifuge (5) was found to be 11.6% by wt where as methanol concentration was 87.7% by wt. and moisture content by Karl-Fischer method was 1.0% by wt. After desired operation time, pressure inside reactor (4) was released through vent (10), vapors were passed to separator (11) where carbon dioxide gas (13) was separated, which can be recycled at (4) from other volatile reaction liquid mixture (12) which was recycled at (4).

After desired stages un-converted methanol, methyl ester, moisture if any, obtained at (4), was sent for recovery having Reboiler-packed tower fractional distillation assembly (14). 1% by wt. of methyl ester sodium-bicarbonate was added in reboiler as stabilizer. Pure methyl ester (15) was separated and stored separately from methanol (16) with or without using vacuum in fractional distillation assembly (14). Pure methanol obtained can be recycled at (1). Highly pure methyl ester fraction was collected, which showed purity of 99.8% by wt on GC analysis and moisture content of 0.03%. The optical rotation of neat liquid methyl ester was measured (−) 8.43 by Polarimeter.

Thus in four stages, more than 97% conversion of calcium lactate into methyl ester was observed.

Example-4

Direct Esterification of Calcium Lactate Solution in Methanol with Carbon Dioxide Using Tri-Ethanolamine at 165° C. at High Pressure (FIG. 1)

110 g dry calcium lactate (1) as mentioned in Example-1, 794 g pure methanol (2) and 110 g tri-ethanolamine (2a) were charged in mild steel high pressure reactor vessel (4) having capacity of 5 L and continuously stirred at 750 RPM using agitator. Carbon dioxide gas from cylinder (3) was used to pressurize the reactor so as to get the initial pressure of 20 Kg/cm². Reaction material was then allowed to heat till 165° C. and maintained at this temperature for 1 hour. During operation, pressure inside reactor gets raised to 61.2 Kg/cm². Reaction mass was then allowed to cool till 25° C. and the reaction mixture was filtered on basket centrifuge (5) at 3000 RPM. Wet cake containing calcium carbonate was allowed to dry in oven at 110° C. (7) and stored (8). Filtrate (9) collected from centrifuge (5) was analyzed for methyl ester and methanol content using Shimadzu made GC-MS Model-QP5000 where as the moisture was measured by Automatic Karl-Fischer, Lab India made instrument. The concentration of methyl ester in filtrate was found to be 9.3% by wt where as methanol concentration was 89.9% by wt and moisture content by Karl-Fischer method was 0.5% by wt. The pressure inside the reactor (4) was released through vent (10) and vapors were passed to separator (11) where carbon dioxide gas (13) was separated, which can be recycled at (4). The other volatile reaction liquid mixture (12) was recycled at (4).

In second stage, filtrate obtained from above said centrifuge (5) was again charged in the same mild steel high pressure reactor (4) and continuously stirred at 750 RPM using agitator. Again carbon dioxide gas (3) was used to pressurize the reactor to 20 Kg/cm². Reaction material was then allowed to heat till 165° C. and was maintained at this temperature for 1 hour. During operation, pressure inside reactor got raised to 59.0 Kg/cm². Reaction mass was then allowed to cool till 25° C. and the reaction mass was filtered on the basket centrifuge (5) at 3000 RPM. Wet cake (6) containing calcium carbonate was allowed to dry in oven (7) at 110° C. and stored (8). Filtrate collected (9) from centrifuge (5) was analyzed for methyl ester, methanol and moisture contents as above. The concentration of methyl ester in filtrate was found to be 10.4% by wt where as methanol concentration was 89.1% by wt. and moisture content by Karl-Fischer method was 0.6% by wt. The pressure inside reactor (4) was released through vent (10) and vapors were passed to separator (11) where carbon dioxide gas (13) was separated, which can be recycled at (4), from other volatile reaction liquid mixture (12) which was recycled at (4).

Example-5

Control Experiment: Reaction of Calcium Lactate Solution in Methanol at 165° C. at High Pressure (FIG. 1)

1100 g dilute calcium lactate (10 by wt %) solution in methanol prepared as explained in Example-2 was charged in mild steel high pressure reactor vessel (4) having capacity of 5 L and continuously stirred at 750 RPM using agitator. Reaction material was then allowed to heat till 165° C. and was maintained at this temperature for 1 hour. During operation pressure inside reactor obtained till 20.2 Kg/cm². Reaction mass was then allowed to cool till 25° C. and was filtered on the basket centrifuge (5) at 3000 RPM. No precipitate was observed in reaction product. Reaction product collected from reactor bottom (9) was analyzed for methyl ester, methanol contents using Shimadzu made GC-MS Model-QP5000. The concentration of methyl ester in filtrate was found to be 0% by wt where as methanol concentration was 100% by wt. Thus it was found that in absence of carbon dioxide there was no formation of methyl ester.

Direct Esterification of Sodium Lactate at High Pressure

Example-6

Figure 4:
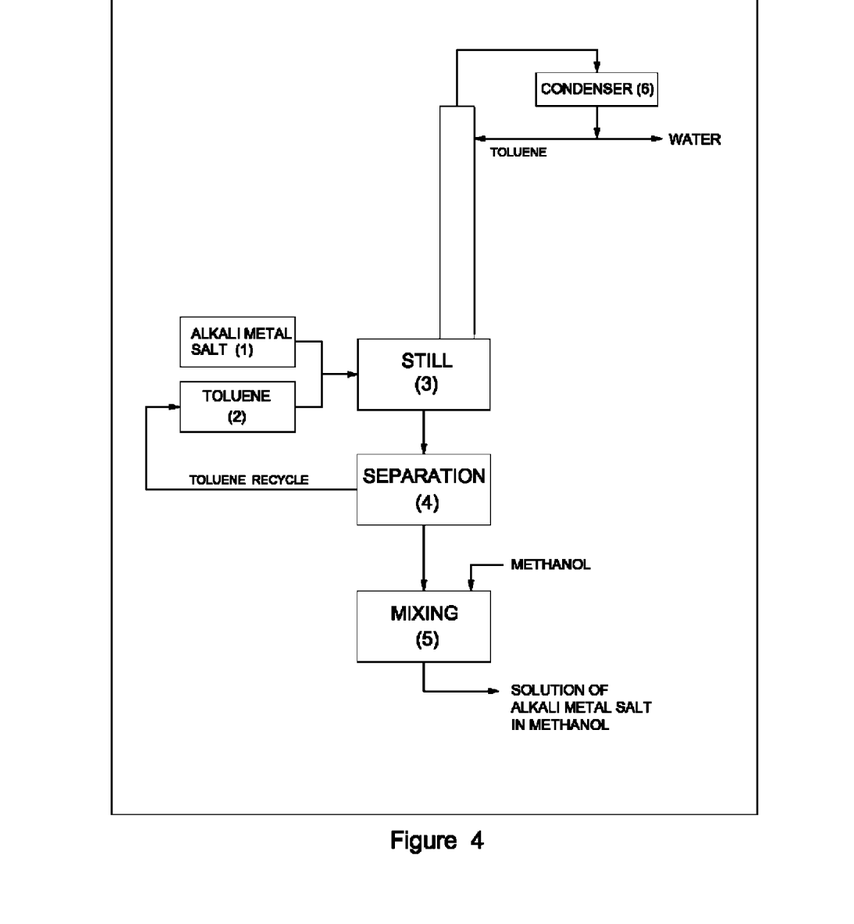
FIG. 4: Process for making anhydrous solution of alkali metal lactate in methanol.

Dehydration of Sodium Lactate Solution in Water (FIG. 4)

Glass vessel-packed tower assembly having capacity 5 L (3) was charged with 2500 g, LACTOCHEM, Chennai (India) made pure sodium lactate solution (1) in water having concentration 70% by wt. along with 1000 g pure toluene (2). The material was then continuously mixed at 250 RPM using agitator. This reactor charge was heated using electric heater. Vapors of water along with toluene rose above through packed tower and got condensed (6) at top to get two layers as distillate. The top and light organic layer was recycled continuously, whereas the bottom aqueous layer was continuously removed till complete exhaustion and no presence of aqueous layer in distillate was seen. Top temperature reached from 85 to 105° C. towards the end of operation and bottom reactor temperature was in the range of 99-105° C. The dehydrated sodium lactate in toluene was transferred to separator (4). The dehydrated sodium lactate in toluene thus obtained was then cooled slowly to 40° C. The top toluene layer was removed by siphoning out of the separator (4). Crystals of sodium lactate obtained at bottom of the reactor were dissolved in 2500 g of pure methanol to make 40% by wt solution of sodium lactate in methanol in mixer (5). The solution of sodium lactate in methanol was cooled to 25° C. and stored. This water free sodium lactate solution in methanol was used in subsequent examples given below.

Example-7

Direct Esterification of Sodium Lactate Solution in Methanol with Carbon Dioxide at 165° C. at High Pressure (FIG.-1)

1100 g (40% by wt) of water free sodium lactate solution (1) in methanol (2) prepared as explained in Example-6 was charged in mild steel high pressure reactor vessel (4) having capacity of 5 L and continuously stirred at 750 RPM using agitator. Carbon dioxide gas from cylinder (3) was used to pressurize the reactor so as to get initial pressure of 28.7 Kg/cm². Reaction material was then allowed to heat till 165° C. and was maintained at this temperature for 1 hour. During operation the pressure inside reactor rose up to 53.5 Kg/cm². Reaction mass was then allowed to cool till 25° C. and was filtered on the basket centrifuge (5) at 3000 RPM. Wet cake (6) containing sodium carbonate was allowed to dry in oven (7) at 110° C. and stored (8). Filtrate collected (9) from centrifuge (5) was analyzed for methyl ester, methanol contents using Shimadzu made GC-MS Model-QP5000 where as the moisture was measured by Automatic Karl-Fischer, Lab India made instrument. The concentration of methyl ester in filtrate was found to be 20.3% by wt where as methanol concentration was 76.9% by wt. and moisture content by Karl-Fischer method was 0.5% by wt. After desired operation time, pressure inside reactor (4) was released through vent (10), vapors were passed to separator (11) where carbon dioxide gas (13) was separated, which can be recycled at (4), from other volatile reaction liquid mixture (12) which was recycled at (4), unconverted methanol, methyl ester, moisture if any obtained at (4), was sent for recovery having Reboiler-packed tower fractional distillation assembly (14). 1% by wt of methyl ester sodium-bicarbonate was added in reboiler as stabilizer. Pure methyl ester (15) was separated and stored separately from methanol (16) with or without using vacuum in fractional distillation assembly (11). Pure methanol obtained can be recycled at (4).

Example-8

Figure 2:
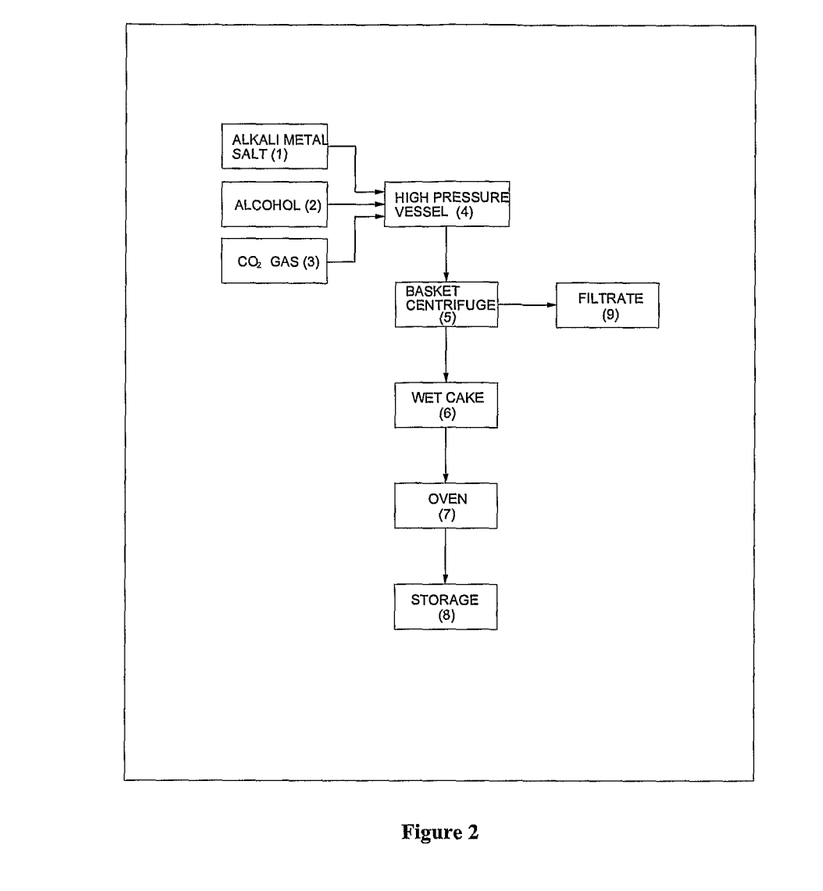
FIG. 2: Batch process for the synthesis of alkyl esters using alkali metal salt of carboxylic acid, alcohol and $CO_2$ gas in high pressure reactor.

Direct Esterification of Sodium Lactate Solution in Methanol with Carbon Dioxide Using Tri-Ethanolamine at 165° C. at High Pressure (FIG.-2)

Water free sodium lactate solution (1) in methanol (2) from as explained in Example-6 was distilled to remove excess methanol so as to get final sodium lactate concentration of 50% by wt., with remaining methanol and trace amount of toluene. 1300 g of such solution (1) was charged in mild steel high pressure reactor (4) having capacity 5 L and was continuously stirred at 750 RPM using agitator. Carbon dioxide gas from cylinder (3) was used to pressurize in reactor so as to get initial pressure 20 Kg/cm². Reaction material was then allowed to heat till 165° C. and was maintained at this temperature for 1 hour. During operation pressure inside reactor obtained till 56 Kg/cm². Reaction mass is then allowed to cool till 25° C. and then removed from reactor bottom followed filtration in basket centrifuge (5). Then the filtrate (9) was subjected to flash distillation in rotavapor so as to remove maximum amount of volatile matters as distillate. Residue collected in rotavapor after distillation was recycled in mild steel reactor along with 900 g pure methanol (2). Reactor bottom sample was analyzed for methyl ester, methanol contents using Shimadzu made GC-MS Model-QP5000 where as the moisture was measured by Automatic Karl-Fischer, Lab India made instrument. The concentration of methyl ester in reactor bottom sample was found to be 15.6% by wt where as methanol concentration was 69.8% by wt. and moisture content by Karl-Fischer method was 0.5% by wt.

In second stage, feedstock taken as mentioned above was processed in same mild steel high pressure reactor (4) and continuously stirred at 750 RPM using agitator. Again carbon dioxide gas (3) was pressurized inside reactor till 20 Kg/cm². Reaction material was then allowed to heat till 165° C. and was maintained at this temperature for 1 hour. During operation pressure inside reactor obtained till 46.5 Kg/cm². Reaction mass was then allowed to cool till 25° C. and then removed from reactor bottom followed by filtration in basket centrifuge (5). Then the filtrate (9) was subjected to flash distillation in Rota vapor so as to remove maximum amount of volatile matters as distillate. Distillate and residue were collected separately. Distillate and reactor bottom sample was analyzed on water free basis for methyl ester, methanol contents using Shimadzu made GC-MS Model-QP5000 where as the moisture was measured by Automatic Karl-Fischer, Lab India made instrument. The concentration of methyl ester in reactor bottom sample was found to be 17.1% by wt where as methanol concentration was 67.1% by wt. and moisture content by Karl-Fischer method was 0.55% by wt. and the concentration of methyl ester in distillate was found to be 40.2% by wt where as methanol concentration was 58.7% by wt. and moisture content by Karl-Fischer method was 0.5% by wt.

Thus it was found that sodium lactate can be converted directly into methyl ester at high pressure reaction and high temperature using methanol and carbon dioxide gas.

Example-9

Direct Esterification of Sodium Lactate Using Methanol And Carbon Dioxide in Presence of Methyl Ester(Methyl Lactate) 165° C. at High Pressure (FIG.-2)

Water free sodium lactate solution in methanol from as explained in Example-6 was distilled to remove excess methanol so as to get final sodium lactate and methanol concentrations of 50% by wt. each. Equal amount of pure methyl ester(methyl lactate), PURAC Inc. USA made, was added so as to get feed stock composition 50% methyl ester, 25% water free sodium lactate (1) and 25% methanol (2) by weight. This mixture was charged in mild steel high pressure reactor (4) having capacity 5 L and continuously stirred at 750 RPM using agitator. Carbon dioxide gas from cylinder (3) was pressurized in reactor so as to get initial pressure 20 Kg/cm². Reaction material was then allowed to heat till 165° C. and was maintained at this temperature for 1 hour. During operation pressure inside reactor obtained till 56.3 Kg/cm². Reaction mass was then allowed to cool till 25° C. and then removed from reactor bottom. Reactor bottom sample was analyzed for methyl ester, methanol contents using Shimadzu made GC-MS Model-QP5000 where as the moisture was measured by Automatic Karl-Fischer, Lab India made instrument. The concentration of methyl ester in reactor bottom sample was found to be 58.4% by wt where as methanol concentration was 40.2% by wt. and moisture content by Karl-Fischer method was 0.7% by wt. Thus sodium lactate can be directly converted to methyl ester and conversion found to be 37-40%.

Direct Esterfication of Calcium Lactate at High Pressure

Example-9

Ethylation of Calcium Lactate at Different Agitation Speed (FIG.-2)

100 g calcium lactate (10 wt %) solution (1) and ethanol (2) was charged in mild steel high pressure reactor vessel (4) having capacity of 5 L and continuously stirred at speed of agitation ranging from 300, 600 and 1000 RPM using agitator. Carbon dioxide gas from cylinder (3) was pressurized in reactor so as to get initial pressure 25 Kg/cm². Reaction material was then allowed to heat till 200° C. and was maintained at this temperature for 8 hour. During operation pressure inside reactor goes up to 72-80 Kg/cm². Reaction mass was then allowed to cool till 25° C. and the reaction mixture was filtered on the basket centrifuge (5) at 3000 RPM. The wet cake (6) obtained from centrifuge; containing calcium carbonate was allowed to dry in oven (7) at 110° C. and stored (8). The filtrate (9) collected from centrifuge was analyzed for ethyl ester, ethanol contents using Shimadzu made GC-MS Model-QP5000 where as the moisture was measured by Automatic Karl-Fischer, Lab India made instrument. The concentration profile of ethyl ester during the reaction was shown in Table 1. The average moisture content at the end of the reaction was found in the range of 7.5% by wt.

TABLE 1

Effect of speed of agitation on % formation of ethyl ester (reaction conditions: calcium lactate 10%; moisture content - 5%; reaction temperature - 200° C., $CO_2$ pressure - 25 kg/cm$^2$; speed of agitation 1000 RPM)

| Time (h) | % formation of ethylation at different speed of agitation | | |
|---|---|---|---|
| | 300 RPM | 600 RPM | 1000 RPM |
| 0.5 | 5.30 | 11.82 | 16.44 |
| 1 | 13.54 | 22.91 | 24.02 |
| 2 | 22.63 | 32.70 | 42.95 |
| 3 | 32.65 | 52.56 | 52.56 |
| 4 | 49.66 | 61.61 | 62.44 |
| 5 | 61.83 | 69.00 | 69.65 |
| 6 | 70.24 | 72.42 | 72.88 |
| 7 | 72.00 | 75.37 | 77.04 |

Example-10

Ethylation Of Calcium Lactate at Different $Co_2$ Pressure (FIG.-2)

100 g calcium lactate (10 wt %) solution (1) and ethanol (2) was charged in mild steel high pressure reactor vessel (4) having capacity of 5 L and continuously stirred at speed of agitation 1000 RPM using agitator. Carbon dioxide gas (3) from cylinder was pressurized in reactor so as to get initial pressure from 5, 15 and 25 Kg/cm$^2$. Reaction material was then allowed to heat till 200° C. and was maintained at this temperature for 8 hour. During ethylation reaction at initial at pressure 5, 10 and 15 kg/cm$^2$, the final overall pressure inside reactor during the reaction goes up to 39, 59 and 80 Kg/cm$^2$ respectively. Reaction mass was then allowed to cool till 25° C. and the reaction mixture was filtered on the basket centrifuge (5) at 3000 RPM. The wet cake (6) obtained from centrifuge; containing calcium carbonate was allowed to dry in oven (7) at 110° C. and stored (8). The filtrate (9) collected from centrifuge was analyzed for ethyl ester, ethanol contents using Shimadzu made GC-MS Model-QP5000 where as the moisture was measured by Automatic Karl-Fischer, Lab India made instrument. The concentration profile of ethyl ester during the reaction was shown in Table 2. The moisture content at the end of the reaction was found 7.8% by wt.

TABLE 2

Effect of $CO_2$ pressure on ethylation of calcium lactate using $CO_2$ (reaction conditions: moisture content 5%; temperature 200° C., calcium lactate 10%; speed of agitation 1000 RPM)

| Time (h) | % formation of ethylation at different initial $CO_2$ pressure | | |
|---|---|---|---|
| | 5 Kg/cm$^2$ | 15 kg/cm$^2$ | 25 kg/cm$^2$ |
| 0.5 | 13.95 | 17.46 | 16.44 |
| 1 | 21.25 | 25.40 | 24.02 |
| 2 | 26.69 | 37.50 | 42.95 |
| 3 | 30.73 | 49.33 | 52.56 |
| 4 | 44.15 | 58.38 | 62.44 |

TABLE 2-continued

Effect of $CO_2$ pressure on ethylation of calcium lactate using $CO_2$ (reaction conditions: moisture content 5%; temperature 200° C., calcium lactate 10%; speed of agitation 1000 RPM)

| Time (h) | % formation of ethylation at different initial $CO_2$ pressure | | |
|---|---|---|---|
| | 5 Kg/cm$^2$ | 15 kg/cm$^2$ | 25 kg/cm$^2$ |
| 5 | 53.76 | 61.59 | 69.65 |
| 6 | 54.41 | 68.17 | 72.88 |
| 7 | 56.70 | 75.28 | 77.04 |

Example-11

Ethylation of Calcium Lactate at Different Initial Concentration of Calcium Lactate Using $Co_2$ and Ethanol (FIG.-2)

The 5%, 10% and 15% initial concentration of calcium lactate solution was prepared by dissolving 50, 100 and 150 g calcium lactate (1) solution in ethanol (2) prepared as explained in Example-2 was charged in mild steel high pressure reactor vessel (4) having capacity of 5 L and continuously stirred at speed of agitation 900 RPM using agitator. Carbon dioxide (3) gas from cylinder was pressurized in reactor so as to get initial pressure 25 Kg/cm$^2$. Reaction material was then allowed to heat till 200° C. and was maintained at this temperature for 8 hour. During operation pressure inside reactor goes up to 72-80 Kg/cm$^2$. Reaction mass was then allowed to cool till 25° C. and the reaction mixture was filtered on the basket centrifuge (5) at 3000 RPM. The wet cake (6) obtained from centrifuge; containing calcium carbonate was allowed to dry in oven (7) at 110° C. and stored (8). The filtrate (9) collected from centrifuge was analyzed for ethyl ester, ethanol contents using Shimadzu made GC-MS Model-QP5000 where as the moisture was measured by Automatic Karl-Fischer, Lab India made instrument. The concentration profile of ethyl ester during the reaction was shown in Table 3. The moisture content at the end of the reaction was found in the range of 6.2% by wt.

TABLE 3

Effect of initial calcium lactate concentration on ethylation using $CO_2$ (Reaction conditions: moisture content 5%; temperature 200° C., $CO_2$ pressure: 25 kg/cm$^2$; speed of agitation 1000 RPM)

| Time (h) | % formation of ethylation at different initial concentration of calcium lactate | | |
|---|---|---|---|
| | 5% calcium lactate | 10% calcium lactate | 15% calcium lactate |
| 0.5 | 14.96 | 16.44 | 20.44 |
| 1 | 42.12 | 24.02 | 31.84 |
| 2 | 55.42 | 42.95 | 44.15 |
| 3 | 64.66 | 52.56 | 58.25 |
| 4 | 71.49 | 62.44 | 60.84 |
| 5 | 82.95 | 69.65 | 61.21 |
| 6 | 83.13 | 72.88 | 64.91 |
| 7 | 84.06 | 77.04 | 66.38 |
| 8 | 85.72 | 79.45% | 69.46 |

Example-12

Ethylation of Calcium Lactates at Different Temperature (FIG.-2)

At start 10% concentration of calcium lactate solution was prepared by dissolving 100 g calcium lactate powder (1) in ethanol (2) prepared as explained in Example-2 was charged in mild steel high pressure reactor vessel (4) having capacity of 5 L and continuously stirred at speed of agitation 1000 RPM using agitator. Carbon dioxide (3) gas from cylinder was pressurized in reactor so as to get initial pressure 25 Kg/cm². The reaction material was allowed to heat from 190° C., 200° C. and 210° C. and was maintained at this temperature for 8 hour. At reaction temperature 190° C., 200° C. and 210° C., the operation pressure inside reactor goes up to 72, 79.6 and 80 Kg/cm² respectively. The reaction mass was then allowed to cool till 25° C. and the reaction mixture was filtered on the basket centrifuge (5) at 3000 RPM. The wet cake (6) obtained from centrifuge; containing calcium carbonate was allowed to dry in oven (7) at 110° C. and stored (8). The filtrate (9) collected from centrifuge was analyzed for ethyl ester, ethanol contents using Shimadzu made GC-MS Model-QP5000 where as the moisture was measured by Automatic Karl-Fischer, Lab India made instrument. The concentration profile of ethyl ester during the reaction was shown in Table 4. The moisture content at the end of the reaction was found in the range of 9% by wt.

TABLE 4

Effect of temperature on ethylation of calcium lactate using ethanol and CO₂ (Reaction conditions: calcium lactate 10%; moisture content 5%, CO₂ pressure 25 kg/cm²; speed of agitation 1000 RPM)

| | % formation of ethylation at different temperatures | | |
|---|---|---|---|
| Time (h) | 190° C. | 200° C. | 210° C. |
| 0.5 | 13.58 | 16.44 | 14.59 |
| 1 | 19.86 | 24.02 | 26.42 |
| 2 | 30.85 | 42.95 | 46.37 |
| 3 | 40.27 | 52.56 | 58.00 |
| 4 | 47.66 | 62.44 | 67.45 |
| 5 | 51.73 | 69.65 | 71.40 |
| 6 | 50.34 | 72.88 | 77.41 |
| 7 | 55.61 | 77.04 | 79.44 |
| 8 | 55.70 | | |

Example-13

Ethylation of Calcium Lactates at Different Moisture Content (FIG.-2)

The % moisture content in the reaction system was varied from 1.5% to 23% by adjusting and analyzing moisture in the calcium lactate and in ethanol. Generally calcium lactate contents 23% moisture at 30° C. Initially calcium lactate (100 g) solution (1) was dissolving in ethanol (2) prepared as explained in Example-2 was charged in mild steel high pressure reactor vessel (4) having capacity of 5 L and continuously stirred at speed of agitation 1000 RPM using agitator.

TABLE 5

Effect of moisture content on ethylation of calcium lactate using ethanol and CO₂ (reaction conditions: calcium lactate 10%; reaction temperature 200° C., CO₂ Pressure - 25 kg/cm²

| | % formation of ethylation at different initial moisture content in calcium lactate | | |
|---|---|---|---|
| Time (h) | 1.5% Moisture | 5% Moisture | 23% Moisture |
| 0.5 | 9.88 | 16.44 | 26.42 |
| 1 | 16.81 | 24.02 | 39.16 |
| 2 | 23.83 | 42.95 | 48.31 |
| 3 | 36.67 | 52.56 | 50.80 |
| 4 | 40.18 | 62.44 | 51.45 |

TABLE 5-continued

Effect of moisture content on ethylation of calcium lactate using ethanol and CO₂ (reaction conditions: calcium lactate 10%; reaction temperature 200° C., CO₂ Pressure - 25 kg/cm²

| | % formation of ethylation at different initial moisture content in calcium lactate | | |
|---|---|---|---|
| Time (h) | 1.5% Moisture | 5% Moisture | 23% Moisture |
| 5 | 43.60 | 69.65 | 51.36 |
| 6 | 51.63 | 72.88 | 51.54 |
| 7 | 53.11 | 77.04 | 52.93 |
| 8 | 64.66 | 79.00 | 53.67 |

Carbon dioxide gas from cylinder (3) was pressurized in reactor so as to get initial pressure 25 Kg/cm². The reaction material was allowed to heat at 200° C. and was maintained at this temperature for 7-8 hour. During operation pressure inside reactor goes up to 72-80 Kg/cm². The reaction mass was then allowed to cool till 25° C. and the reaction mixture was filtered on the basket centrifuge (5) at 3000 RPM. The wet cake (6) obtained from centrifuge; containing calcium carbonate was allowed to dry in oven (7) at 110° C. and stored (8). The filtrate (9) collected from centrifuge was analyzed for ethyl ester, ethanol contents using Shimadzu made GC-MS Model-QP5000 where as the moisture was measured by Automatic Karl-Fischer, Lab India made instrument. The concentration profile of ethyl ester during the reaction was shown in Table 5. The moisture content at the end of the reaction was found in the range of 6-15% by wt.

Continuous Esterification of Sodium Lactate at Atmospheric Pressure

Example-14

Figure 3:
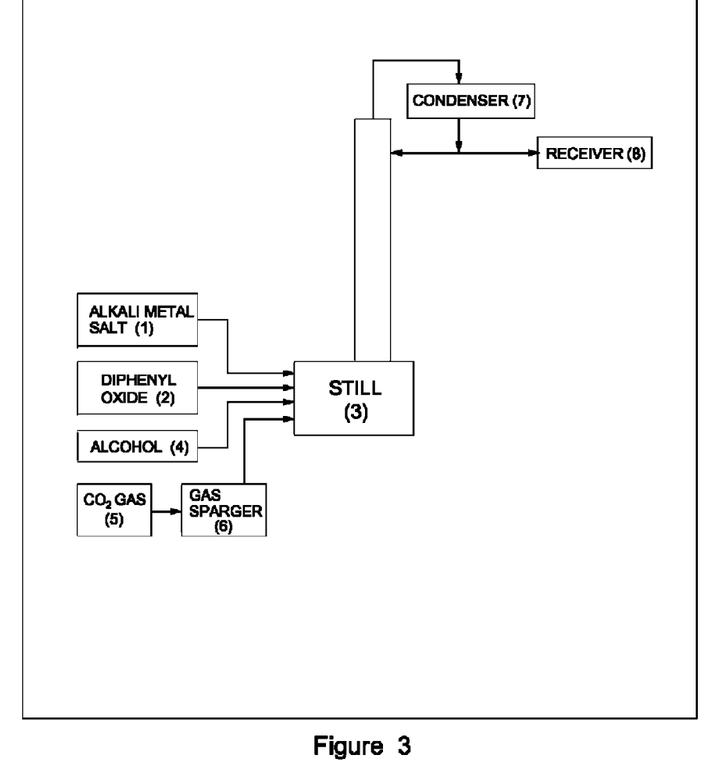
FIG. 3: Continuous process for the synthesis of alkyl esters using alkali metal salt of carboxylic acid, alcohol and $CO_2$ gas at atmosphere pressure.

Direct Esterification Sodium Lactate Using Methanol, Carbon Dioxide and Di-Phenyl Oxide as Heating Medium at 165° C. & Atmospheric Pressure (FIG.-3)

Glass vessel-packed tower assembly having capacity 5 L was charged with 3300 g, LACTOCHEM, Chennai (India) made pure sodium lactate solution in water having concentration 70% by wt. along with 1200 g pure toluene. The material was then continuously mixed at 250 RPM using agitator. This reactor charge was heated using electric heater. Vapors of water along with toluene rose above through packed tower and got condensed at top to get two layers as distillate. The top and light organic layer was recycled continuously to the distillation still, whereas bottom aqueous layer was continuously removed till there were no traces of aqueous layer in distillate. Top temperature reached 105° C. towards end of operation and bottom reactor temperature was 105° C. Thus dehydrated sodium lactate in toluene was obtained which was then cooled slowly to 60° C. The top toluene layer was then removed by siphoning. Crystals of sodium lactate were obtained at bottom of reactor. The dehydrated sodium lactate (1) along with trace amount of toluene was charged in mild steel high pressure reactor vessel (3) having capacity of 5 L along with 800 g of di-phynyl oxide (2) and continuously stirred at 750 RPM using agitator. The reactor charge was then heated till 165° C. and was maintained at this temperature through out the reaction. Pure methanol (4) was passed through sparger at bottom of reactor at the rate of 200 g/h. Similarly, carbon dioxide gas (5) was also passed simultaneously from bottom of the reactor through separate gas sparger (6) at the rate of 40 L/h. Vapors of un-reacted methanol, methyl ester formed and un-reacted carbon dioxide gas rose through reactor; methyl ester and menthol got condensed in condenser (7) and collected in receiver (8) as distillate. This operation was continued for 5 hours. Distillate collected was analyzed for methyl ester in GC-MS. Distillate showed 24.5% by wt of methyl ester by wt.

Example-15

Preparation of Methyl Acetate from Sodium Acetate Using Methanol, Carbon Dioxide at 170° C. and at High Pressure 82 gm of anhydrous Sodium acetate (technical grade) was charged in an autoclave and to it 1200 gm methanol was charged. The reaction mixture was pressurized with Carbon dioxide to 210 psig, and the reaction mixture was heated to 130° C. was maintained at this temperature for 8 hours. The pressure of reaction mixture went up to 620 psig and came down to 570 psig. Then the reaction mixture was pressurized with carbon dioxide to 620 psig and then the reaction mixture was heated to 170° C. was maintained at this temperature for additional 8 hours and then cooled. The reaction mixture weighed as 1215 gm and was subjected to analysis by Gas Chromatograph-Mass Spectrophotometer and showed 60 gm of methyl acetate in the reaction mixture.

Example-16

Preparation of Methyl Benzoate from Sodium Benzoate Using Methanol, Carbon Dioxide at 170° C. & at High Pressure 250 gm of anhydrous Sodium benzoate (technical grade) was charged in an autoclave and to it 1500 gm methanol was charged. The reaction mixture was pressurized with carbon dioxide to 250 psig, and the reaction mixture was heated to 170° C. was maintained at this temperature for 8 hours. The pressure of reaction mixture went up to 950 psig and came down to 850 psig at the end of reaction. On cooling the reaction mass to room temperature the pressure came down to 120 psig. The reaction mixture weighed as 1450 gm and was subjected to analysis by Gas Chromatograph-Mass Spectrophotometer and showed 140 gm of methyl benzoate in the reaction mixture.

Example-17

Continuous Methyl Benzoate Production from Sodium Benzoate Using Methanol, Carbon Dioxide and Di-Phenyl Oxide as Heating Medium at 170° C. & at Atmospheric Pressure (1.03 KG/CM$^2$)

The five liter SS autoclave was charged with 576 gm of anhydrous sodium benzoate along with 1500 gm of diphenyl oxide. The reaction mixture was heated under nitrogen current at 120° C. for three hours to remove traces of moisture. Then the reaction mixture was heated to 165 to 170° C. and to it the methanol addition at the rate of 120 ml/h along with simultaneous addition of carbon dioxide at the rate of 40 L/h was done. The distillate along with product was cooled by water cooled condenser and was collected. Total methanol addition was 746 gm and the carbon dioxide added was about 352 gm in about 8 hours. The distillate collected weighed about 650 gm and showed 195 gm of methyl benzoate in it (by Gas Chromatograph-Mass spectroscopic analysis).

Example-18

Preparation of Methyl Salicylate from Sodium Salicylate Using Methanol, Carbon Dioxide at 170° C. & at High Pressure 80 gm of anhydrous sodium salicylate (technical grade) was charged in an autoclave and to it 1500 gm methanol was charged. The reaction mixture was pressurized with carbon dioxide to 260 psig, and the reaction mixture was heated to 170° C. was maintained at this temperature for 8 hours. The pressure of reaction mixture went up to 955 psig and came down to 900 psig. The reaction mixture was cooled and was pressurized with carbon dioxide to 250 psig & it was heated at 170° C. for further 8 hours. The reaction mixture was cooled. The reaction mixture 1457 gm after work-up was subjected to gas chromatograph-mass spectrophotometer analysis. The reaction mixture showed 42 gm of methyl salicylate and around 4 gm of phenol as the by-product.

Figure 5:
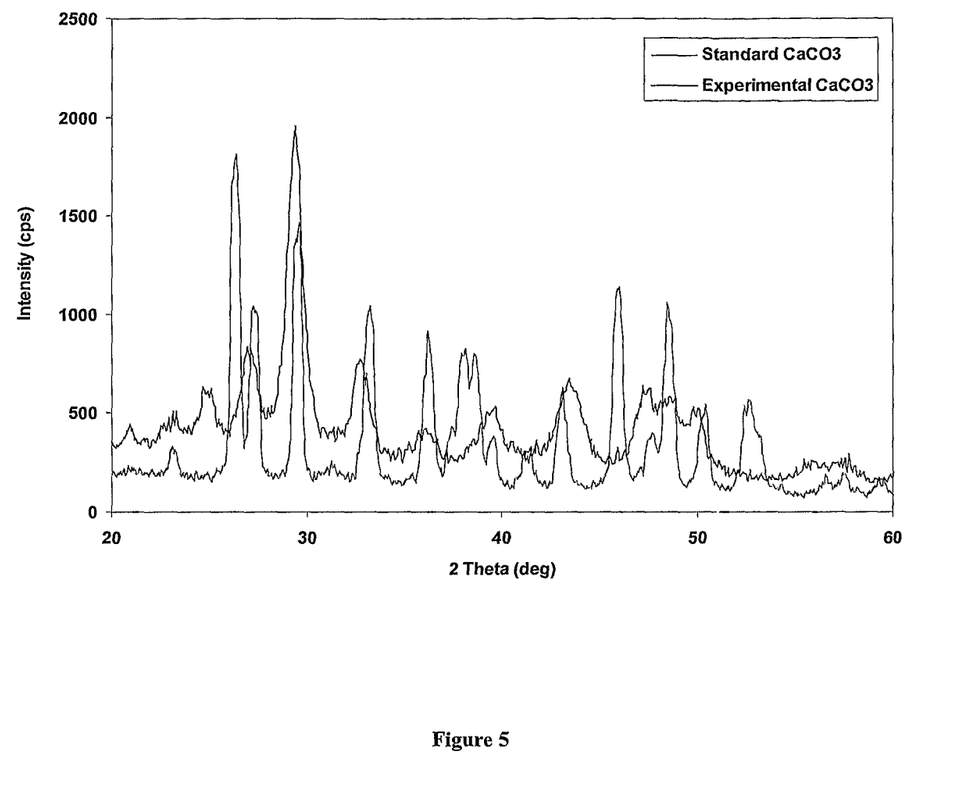
FIG. 5: The XRD pattern of standard calcium carbonate sample and the one prepared by the esterification of alkali metal salt of carboxylic acid using $CO_2$ and alcohol.

Characterization of Byproducts Calcium Carbonate (FIG. 5)

The direct esterification of calcium lactate with $CO_2$ and alcohol produces highly pure alkyl esters with calcium carbonate as byproduct. The synthesized byproduct namely calcium carbonate sample was characterized for its crystallinity, surface area and pore volume. The merit of this route is that the synthesized byproduct can be recycled into the fermentator to make corresponding alkali metal lactate or the finely precipitated calcium carbonate can be used for various other applications. The unreacted calcium lactate was removed by addition of excess alcohol and the resulting solid mass was allowed to dry in oven at 100° C. The dry weight of calcium carbonate was measured and subsequently the material balance of the reaction was also verified. The experimental error was found to lie within ±5%. FIG. 4 shows the XRD pattern of standard calcium carbonate sample and the one prepared by the esterification of calcium lactate using $CO_2$ and alcohol. As can be seen the phase of the synthesized calcium carbonate was well-crystallized calcite with a hexagonal structure (JCPDS 83-0577 and 83-1762) and match with the authentic calcium carbonate sample. The results of BET surface area and pore volumes obtained by multi point adsorption method are presented in Table 6 and show that the calcium carbonate prepared ($CaCO_{3\,synthesized}$) in the present process gives higher specific surface area than the commercial calcium carbonate ($CaCO_{3\,commercial}$) sample indicating that particle size of synthesized calcium carbonate in the present study is much smaller than that of commercial calcium carbonate. The $CaCO_{3\,synthesized}$ shows higher pore volume as well as average pore size as compared to $CaCO_{3\,commercial}$.

TABLE 6

BET surface area, pore size and pore volume of calcium carbonate

| Sr. No | surface area (m$^2$/g) | Pore volume (cm$^3$/g) | Avg. pore size (Å) |
|---|---|---|---|
| CaCO$_3$-commercial | 16.10 | 0.0618 | 153.5 |
| CaCO$_{3\text{-}synthesized}$ | 65.21 | 0.308 | 189.1 |

Advantages Of The Present Invention

The method of direct esterification reaction reported in this invention is from calcium or sodium lactate to methyl ester and thus obviates the objectionable pollutant such as calcium sulfate or sodium sulfate obtained in traditional methods.

In the present invention, calcium or sodium carbonate or bi-carbonate formed as byproduct along with methyl ester during reaction, which can be recycled back to fermentation section.

In present novel process, excess, un-reacted methanol and carbon dioxide obtained can be easily separated and recycled back in the operation.

The use of reagent reported in this invention, such as triethanolamine increases conversion of sodium or calcium lactate to methyl ester.

In this invention, there is no side product formation.

The superheated methanol vapors fed in the reactor bottom helps to remove water, if present; methyl ester formed towards top of the reactor, and thus arrests the reversible reaction which in turn helps to enhance the forward reaction sodium lactate to methyl ester in continuous operation at atmospheric pressure. The net effect of the above-mentioned operation is to get the higher conversion of sodium lactate to methyl ester is achieved.

The continuous method reported in this invention permits molar ratio of 8. The methyl ester produced by this invention has the quality of 99.5 to 99.8% by wt purity of GC-MS and has very low moisture content of 0.03-0.5% by wt.

The novel methods reported in this invention can be viable commercially. The processes reported in this invention are safe to operate and easy to control on large scale, thus it makes process commercially viable. Thus in the methods of this invention, as compared to the usual and traditional methods, extremely high quality goods are obtained in high yields and highly pure methyl ester can be produced.

We claim:

1. A process for the preparation of optically pure alkyl esters by esterification of alkali metal and alkaline earth metal salts of carboxylic acid selected from the group consisting of acetates, lactates, salicylates and benzoates, using alcohol and $CO_2$ and the said process comprising the steps of:
   i. mixing dehydrated metal carboxylate salt powder with alcohol for period in the range of 15 minutes to 30 minutes with stirring in the range of 500 to 1000 rpm to obtain 5-30% by wt solution of metal carboxylate salt in alcohol;
   ii. pressurizing the solution as obtained in step (i) with carbon dioxide in the range of 5-60.4 $Kg/cm^2$ at temperature in the range of 145 to 210° C. for period in the range of 15 minutes to 1 hour to obtain a precipitate of alkyl ester and byproducts selected from the group consisting of alkali metal carbonate or bicarbonate;
   iii. separating the precipitates obtained in step (ii) by filtration;
   iv. repeating the steps (i) (ii) and (iii) 3 to 4 times; and
   v. recovering the alkyl ester by distillation with purity in the range of 99.50 to 99.8% by wt. with about 0.03-0.1% by wt of moisture, and recovering the unreacted alcohol and recycling the unreacted alcohol in step iv.

2. A process as claimed in step (i) of claim 1, wherein alcohol used is selected from the group consisting of methanol, ethanol and butanol.

3. A process as claimed in step (i) of claim 1, wherein metals are selected from the group consisting of sodium, potassium or calcium.

4. A process as claimed in claim 1, wherein optical purity of alkyl esters is ranging between 98 to 99%.

5. A process as claimed in claim 1, wherein process is carried out in batch or continuous modes in the absence of mineral acid.

6. A process as claimed step (v) of claim 1, wherein recycled alcohol used for the process in step (iv) is in the mole ratio of 2.8:1 to 4:1, with alkali metal salt.

7. A process as claimed in claim 1, wherein conversion percentage of metal carboxylate salt into alkyl esters is in the range of 95 to 99%.

8. A process as claimed in claim 1, wherein yield of the reaction is ranging between 90 to 99.0% and the selectivity of the reaction towards alkyl esters is greater than 99.0%

9. A process as claimed in claim 1, wherein the precipitate obtained in (iii) is recycled in a fermentation section to obtain said alkali metal salt from a glucose source.

10. A process as claimed in claim 6 wherein recycled alcohol used for the process in step (iv) is in the mole ratio of 2.8 to 1 with alkali metal salt.

* * * * *